United States Patent [19]

Chaiken et al.

[11] Patent Number: 4,971,853
[45] Date of Patent: Nov. 20, 1990

[54] LASER DIRECTED CHEMICAL VAPOR DEPOSITION OF TRANSPARENT METAL FILMS

[75] Inventors: Joseph Chaiken, Syracuse; Daniel T. Rooney, Liverpool; David F. Negrotti; Daniel J. Macero, both of Syracuse, all of N.Y.

[73] Assignee: Syracuse University, Syracuse, N.Y.

[21] Appl. No.: 190,020

[22] Filed: May 4, 1988

[51] Int. Cl.⁵ ............ B32B 3/00; B32B 15/04; B05D 3/06
[52] U.S. Cl. .................... 428/172; 427/53.1; 427/109; 427/250; 428/336; 428/457
[58] Field of Search ........... 430/945; 427/53.1, 109, 427/250; 428/457, 336, 156, 172

[56] References Cited

U.S. PATENT DOCUMENTS 4,022,928  5/1977  Piucyzk ................ 430/945 X
4,701,592 10/1987  Cheung ................ 427/53.1 X

OTHER PUBLICATIONS

Tierney et al., Transparent Metal Microstructures, J. Phys. Chem. 1989, vol. 3, pp. 2880–2882, Apr. 20, 1989.

Primary Examiner—Thomas J. Herbert
Attorney, Agent, or Firm—Wall and Roehrig

[57] ABSTRACT

A thin platinum film which is both conductive and transparent is produced by laser chemical vapor deposition of a suitable organometallic compound, such as allyl cyclopentadienyl platinum. After deposition, the film is annealed to increase the relative abundance of platinum with respect to carbon. The film can be further conditioned by electrically cycling the same in a bath of sulfuric acid.

20 Claims, 2 Drawing Sheets

LASER DIRECTED CHEMICAL VAPOR DEPOSITION OF TRANSPARENT METAL FILMS

BACKGROUND OF THE INVENTION

This invention relates to the depositing of films of metal, for example, by laser chemical vapor deposition. The invention also relates to an improved metal-film electrode which is both highly conductive and highly transparent to light in the ultraviolet, visible, and near infrared spectra. The invention is more specifically directed to a highly transparent electrically conductive metal film that can be used for spectroscopy and for electrochemical, catalytic, charge-transfer, and photochemical processes at electrode surfaces.

Light-transmitting platinum films have been prepared, for example, by photoelectrodeposition onto indium phosphide semiconductor phosphates from dilute aqueous perchloric acid solutions of platinum oxide. Because a wet process is used in making these films, they have low physical strength. Also, because photo-electrodeposition is used, the process is clearly limited to conducting substrates. Semi-transparent platinum films have been produced, limited to a thickness of about 10 nm, by the use of RF/DC sputtering. Previous processes employing laser chemical vapor deposition have produced platinum films but these have not been both conductive and transparent.

OBJECTS AND SUMMARY OF THE INVENTION

Accordingly, it is an object of this invention to produce a metal film which is physically thick enough for use as an electrode to which conductors such as copper wires can be bonded, and which is also highly transparent, i.e. which can be considered "optically thin".

It is a more specific object of this invention to provide a metal film electrode having an optical transmittance of 70% or better.

It is another object of this invention to provide a film having a thickness range in the order of 20–80 nanometers, and thus able to handle significant currents without loss of power or signal.

It is still another object of this invention to provide a transparent, conductive electrode which is robust and persistent, i.e., which is not eroded or rubbed away by physical or most chemical contact with other substances.

In accordance with an aspect of this invention, a highly transparent electrically conducting metal film, e.g., a platinum film, is created by laser directed chemical vapor deposition onto a suitable substrate, such as a quartz wafer. The substrate is positioned within a deposition chamber, and a suitable compound of the metallic element is introduced as a vapor. In one preferred embodiment, this vapor is gaseous allyl cyclopentadienyl platinum. A portion of the surface of the substrate is irradiated with a laser beam that has a wavelength selected to cause photochemical decomposition of the compound. The metallic element, i.e., elemental platinum, is deposited as a film onto the irradiated part of the substrate surface. After deposition, the substrate and the deposited film are annealed by heating the same in an annealing furnace in the presence of air or another suitable oxidizing gas. At this point, the film is highly transmittive (i.e., 70% or better) and also has very good conductivity.

To render the film suitable for use as an electrochemical electrode, the deposited and annealed metal film is cycled electrically while in an acid electrolyte bath. By cycling, it is meant that an electrical current is applied between the film and the bath, alternating between about $\pm 1$ volt. The technique of this invention is suitable not only for platinum deposition, but for deposition of other noble and refractory metals, such as gold, silver, palladium, iridium, and the like. In fact, this technique can be applied to any metal for which there is a suitable compound which can be converted to elemental metal by laser irradiation.

The metal film of this invention, when studied by a scanning electron microscope (SEM) technique or by a Scanning Auger Multiprobe analysis, is seen to have a microstructure characterized by a multiplicity of voids. This porous microstructure is believed to come about because the laser irradiation produces atomic platinum excited states where the photodissociation occurs at the substrate surface. Platinum microcrystals then tend to have different preferred growth sites, depending on the excitation level of the platinum atoms, and this creates a non-uniform surface characterized by deep voids between microcrystal structures.

The substrates can be used as laser exit windows or entrance windows for the deposition chamber. At the exit window, the metal film deposition has a more or less uniform macrostructure. However, at the entrance window, the film macrostructure is characterized by rings, which are believed to be the result of laser beam diffraction and refraction from defects within the substrate.

The above and many other objects, features, and advantages of this invention will be more fully understood from the ensuing description of a preferred embodiment, when considered in connection with the accompanying drawing.

DETAILED DESCRIPTION OF A PREFERRED EMBODIMENT

Figure 1:
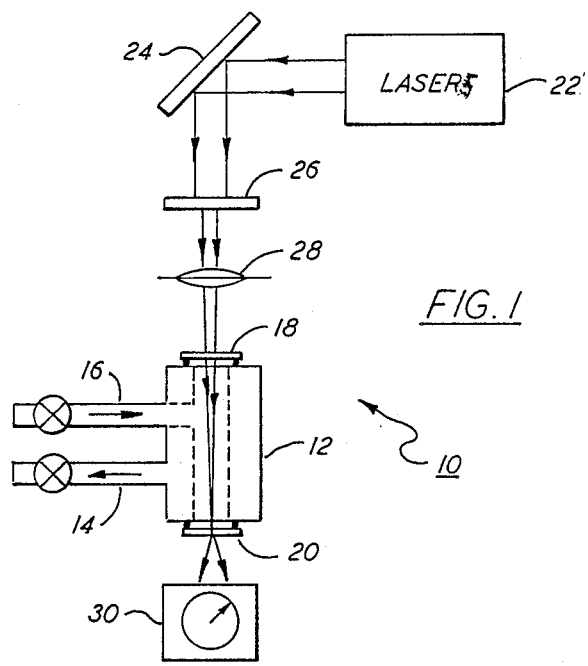
FIG. 1 is a schematic view of laser chemical vapor deposition apparatus for carrying out the method of one embodiment of this invention.

With reference to the drawing, and initially to FIG. 1 thereof, a laser-directed chemical vapor deposition apparatus 10 includes a deposition chamber 12 that has a vacuum port 14 connected to a vacuum pump (not shown) and an input source 16 which supplies or generates a metal compound vapor to the interior of the deposition chamber 12. In the preferred mode, this metal compound vapor is allyl cyclopentadienyl platinum. An entrance substrate 18 of a transparent material (e.g., quartz) is located on an entrance side of the chamber 12, while an exit substrate 20 which can be of the same or different material, is located on the side of the chamber 12 opposite the entrance substrate 18. The exit substrate 20 need not be transparent, and thus can be any suitable dielectric, semiconductor, or conductor. This can include quartz ($SiO_2$), silicon (Si), alumina ($Al_2O_3$), etc. The apparatus 10 further includes a laser 22 that generates a beam of light suitable for isolating the platinum metal from the allyl cyclopentadienyl platinum vapor. The laser 22 produces a pulsed excimer laser beam. The laser pulse rate is at approximately 10 Hz at an energy of 20 mJ per pulse. The beam from the laser 22 is reflected by a mirror 24 through an aperture plate or mask 26, and thence through the entrance and exit substrates 18 and 20 of the chamber 12. An optional focusing lens system 28 is shown here, although it is not necessary for many applications. The laser beam intensity exiting the exit substrate 20 can be measured with a power meter or other sensor 30.

The laser deposition process produces a film on the surfaces of the substrates 18 and 20 ranging in thickness, e.g. from about 20 nm to about 80 nm. The amount of deposition depends on laser power, irradiation time, chemical pressure and substrate temperature. Suitable depositions were produced both at room temperature and at an elevated temperature (50 degrees C. ±10 degrees C.). Deposition times ranged from forty minutes to two hours, although the times could be longer or shorter depending on other conditions.

After deposition, the substrates 18 and 20 with their deposited films 32 and 34, respectively, are further conditioned by annealing in a suitable annealing oven 36. In this case, the annealing takes place with the films 30 and 32 exposed to air, and with the oven being heated to a temperature of 560 degrees C. to 650 degrees C. An electrical heater 38 fed from a controlled power source 39 provides even heat within the furnace 36. In a practical embodiment, the films 32 and 34 were heated for approximately a half hour until the oven temperature reached 560 degrees C. This temperature was maintained for about one hour, after which the oven heater 38 was shut off, and the films 32 and 34 were permitted to cool for approximately five hours.

The annealing process improves the transparency as well as the conductivity of the films 32 and 34.

The deposited metal films 32 and 34 occurred only on the irradiated portions of the entrance and exit substrates 18 and 20. When the substrates 18 and 20 were first removed from the chamber 12, the platinum films 32 and 34 were dull and generally brownish in color. The brown material was sometimes intermixed with black material, which indicated the presence of carbonaceous material. After annealing, however, all the films 32 and 34 had a shiny, metallic appearance. The optical properties of the films also changed dramatically after annealing and were characterized by a 40% increase in transmission.

Using an Auger depth profile on the films 32 and 34, the relative percentages of platinum and carbon were found to be Pt-10%, C-90% before annealing, and Pt-70%, C-30% after annealing. The annealing process was also effective in reducing carbon content in rather thick films.

After annealing, the films were found to have a reflectivity of approximately 10% of He-Ne laser light at 6328 angstroms. The annealing treatment increased film transparency dramatically. For example, the percent transmittance for the thin films 32, 34 increased from about 25% to about 70% at a wavelength of 300 nm, which represents the minimum transmittance for the annealed film. The annealed films were also found to have a resistivity of 72±12 micro-ohm centimeters, as compared to the resistivity of bulk platinum of 10.1 micro-ohm centimeters. The unannealed film had a resistivity of about 1200±200 micro-ohm centimeters, as compared to that of bulk carbon of 1375 micro-ohm centimeters.

Figure 3:
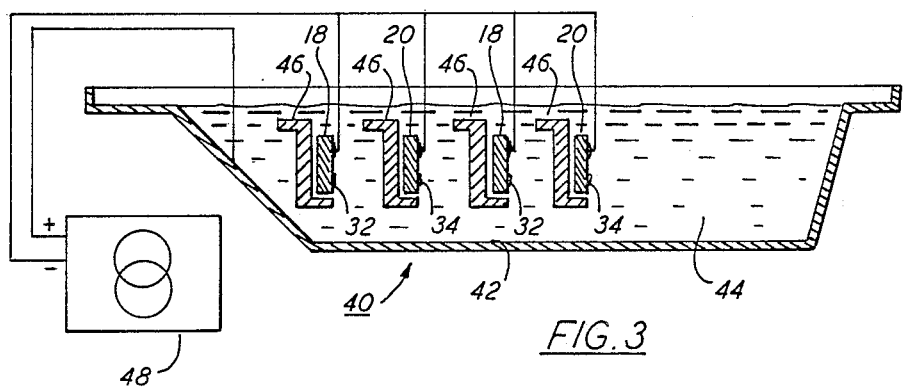
FIG. 3 schematically illustrates the electrical cycling of the deposited film and substrates in an acid bath.
Figure 2:
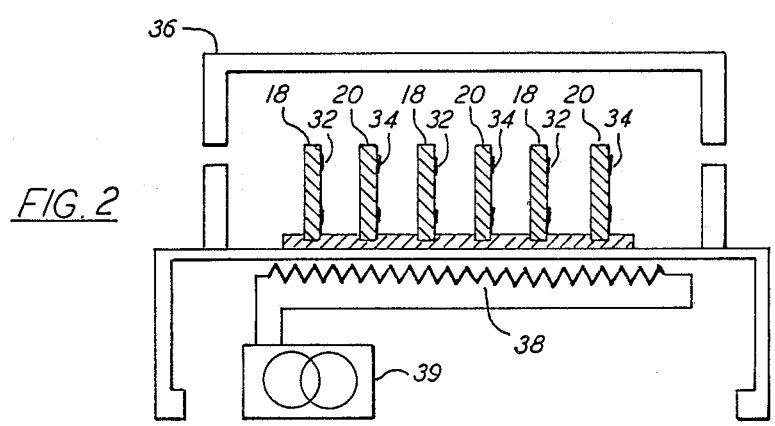
FIG. 2 is a schematic illustration of an annealing furnace for use in this invention.

For electrochemical applications, the platinum film electrodes were further prepared by immersing the same in a cycling bath 40 as shown in FIG. 3. The bath comprises a tank 42 containing an aqueous acid solution 44. In this embodiment, the bath 44 was 0.5 to 1.0 mol aqueous sulfuric acid solution. A number of carriers 46, holding a number of the substrates 18 and 20, are immersed in the solution 44 and a current source 48 applies cycling current between the bath 44 and the substrates 32, 34. The electric current is cycled a number of times between an applied voltage of about plus one volt and minus one volt. After this acid cycling treatment, the films 32 and 34 were found to be sufficiently leached of impurities to serve as electrodes equivalent to standard platinum disc electrodes. Typically, the electrodes were cycled for fifteen minutes at a scan rate of two hundred mv/sec.

In addition to being highly transparent and conductive, platinum films formed in the above manner are quite strong and durable. A test was applied, which involves dragging an ordinary pencil eraser under firm hand pressure across the surface of the film disc 32 or 34. No rubbing away of the electrode film was detected; however, if this test is performed on a platinum film deposited by sputtering or other techniques, the film is easily rubbed away.

The platinum films 32 and 34 have been examined using scanning electron microscopy, and the results are as shown in FIGS. 4A-4C and 5A-5C respectively.

Figure 4A:
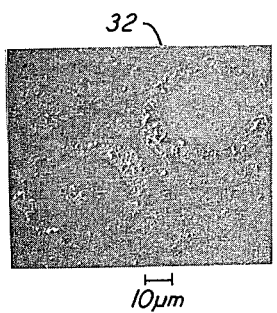
FIGS. 4A–4C are scanning electromicrographs of a platinum film deposited on an entrance substrate, in accordance with this invention.

Referring to FIG. 4A, the entrance substrate film 32 as seen with a scanning electron microscope having a viewing angle of 45 degrees is shown. Here a ring structure appears which is believed to be caused by imperfections in the quartz substrates interacting with the coherent laser light. There is more metal deposited on-ring, where there is apparently a higher beam intensity, and less metal deposited off-ring, where the intensity is lower. This ring structure (here shown to have a diameter of about 30 microns) can be useful in producing ring electrodes, e.g., for specialized high-speed solid state devices.

Figure 5A:
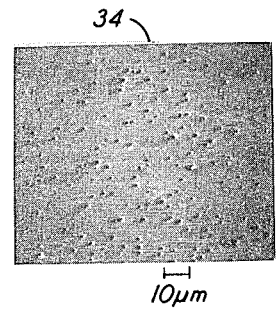
FIGS. 5A–5C are scanning electron micrographs of a platinum film deposited on an exit substrate in accordance with this invention.

As shown in FIG. 5A, the exit substrate film 34 appears to have a more or less even macrostructure. There are nodules scattered across the surface of the exit substrate 34, which are believed to be crystals of pure platinum. These also appear on the film 32 as shown in FIG. 4A.

Figure 4B:
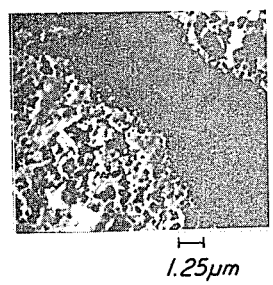
Figure 5B:
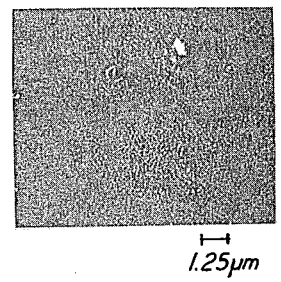

As shown in FIGS. 4B and 5B, most of the films 32 and 34, when enlarged to the scale shown, have a "spongy" texture characterized by micropores running through the films. When further enlarged to the scale shown on FIGS. 4C and 5C, the films 32 and 34 exhibit pores having a diameter of approximately 0.2 microns (200 nm). The dark regions, visible in the highest magnification micrographs (FIGS. 4C and 5C), correspond to places where the films 32, 34 are so thin that the probe beam penetrates to the $SiO_2$ substrate. These dark regions correspond to films that are significantly thinner than 10 nm and which may or may not be continuous.

The high porosity of these films 32, 34 seems to occur, at least in part, because of the annealing process, and is believed to lead to the transparency of the films.

Figure 4C:
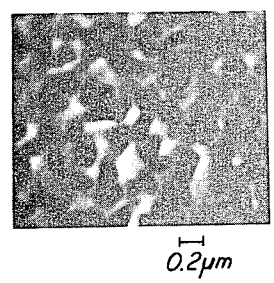
Figure 5C:
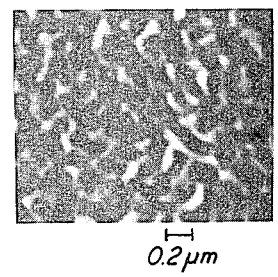

The porous microstructure as exhibited in FIGS. 4C and 5C is also believed to result from the metal atoms being in an excited atomic state at the instant they bond with platinum clusters at nucleation sites. In other techniques, such as sputtering, metal atoms have sufficient time to electronically relax, such as decay to the ground state as in fluorescence during their time of flight from the bulk of the source to the substrate. The film builds up by coalescing ground state metal atoms to produce an even, homogeneous layer. On the other hand, it has been rather definitely shown that organo-metallic compounds can be dissociated with nanosecond laser pulses to produce excited-state metal atoms. These excited-state metal atoms can have enhanced sticking coefficients for a given crystal face as compared with the sticking coefficient for ground state metal atoms and the same crystal face. Thus, the microstructure of FIGS. 4C and 5C is believed to result from preferential growth along certain crystal planes or faces on the given substrates.

Figure 6:
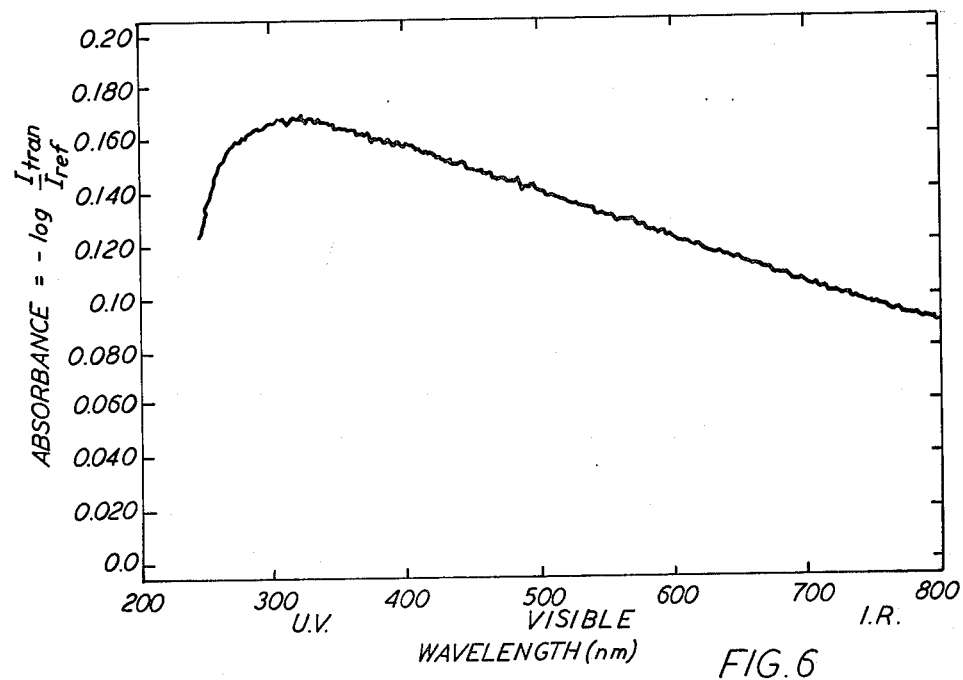
FIG. 6 is a chart of UV and visible absorbence spectrum of a thin annealed platinum film deposited in accordance with this invention.

An absorbence measurement was taken of a thin platinum film 34 prepared according to this invention. The results, as shown in FIG. 6, compare the amount of light transmitted through the film and associated substrate with the amount transmitted through a clean virgin substrate using the same absorbence measuring instrument at the same wavelength. The highest absorbence, i.e., the lowest transmittance, occurs at about 300 nm, and is even more absorbent throughout the visible and UV spectral regions. The peak absorbence of between 0.160 and 0.180 corresponds to about a 70% transmittance.

Annealing in air at 560 degrees C. increases the relative abundance of platinum with respect to carbon. It appears that the loss of carbon associated with annealing is caused by chemical reactions of carbon with gaseous oxygen, thereby liberating the carbon in the form of carbon monoxide and carbon dioxide vapors. Insignificant loss of platinum occurs during the air annealing process.

Annealing can also be carried out in other atmospheres, e.g., ten percent oxygen in argon, or pure oxygen annealing followed by annealing in hydrogen. While air annealing seems to produce optimal results for platinum, other annealing atmospheres and temperatures can be used to obtain optimal results for films of other metals, such as iridium, gold, silver, rhodium, palladium, cadmium, or the like.

The films produced according to this invention can serve as electrochemical electrodes. The electrodes are easy to fabricate and can be electrochemically conditioned simply by cycling cathodically and anodically in sulfuric acid. The fabrication techniques according to this invention may also be used to produce two-dimensional and linear microelectrode arrays, e.g., for charge-coupled devices (CCDs) or similar devices, by employing direct laser writing techniques. This can avoid expensive and difficult ion beam etching techniques.

While this invention has been described in detail with respect to a preferred embodiment, it should be understood that the invention is not limited to that embodiment. Rather, many modifications and variations would present themselves to those of skill in the art without departing from the scope and spirit of this invention, as defined in the appended claims.

What is claimed is:

1. A substrate and a highly transparent electrically conductive metal film electrode formed on said substrate,
    (a) said substrate being formed of a suitable dielectric material; and
    (b) said metal film having a transmissivity for light in the visible spectrum on the order of 70% or higher and an electrical conductivity approximately the bulk conductivity on said metal,
    wherein said metal film has a microstructure that is formed of microcrystals of said metal having preferred growth direction along various crystal planes.

2. The substrate and metal film of claim 1, wherein said metal film has at least one ring formed therein of substantially thicker metal than areas of the film immediately adjacent thereto.

3. The substrate and metal film of claim 1, wherein said substrate comprises $SiO_2$.

4. The substrate and metal film of claim 1, wherein said substrate is transparent.

5. The substrate and metal film of claim 1, wherein said metal film is of a thickness of several hundred nanometers.

6. The substrate and metal film of claim 1, wherein said metal film has a microstructure characterized by a multiplicity of voids that have a diameter on the order of 200 nanometers.

7. A substrate and a highly transparent electrically conductive metal film electrode formed on said substrate,
    (a) said substrate being formed of a suitable dielectric material; and
    (b) said metal film having a transmissivity for light in the visible spectrum on the order of 70% or higher and an electrical conductivity approximately the bulk conductivity of said metal, wherein
    said metal film has a microstructure characterized by a multiplicity of voids that have a diameter on the order of 200 nanometers, and wherein
    said microstructure is further formed of microcrystals of said metal having preferred growth directions along various crystal planes.

8. Method of producing a highly transparent electrically conducting metal film by laser directed chemical vapor deposition such that the metal film has a microstructure formed of microcrystals of the metal having preferred growth directions along various crystal planes, the method comprising
    positioning at least one suitable substrate within a deposition chamber;
    introducing into the chamber a suitable compound of a metallic element as a vapor, wherein the compound provides an adequate vapor pressure for deposition and dissociates under action of light irradiation;
    irradiating a predetermined portion of the surface of the substrate with a laser beam having a wavelength selected to cause photochemical reduction of said compound so that said metallic element is deposited as a metal film of said microcrystals on said predetermined portion of the substrate surface; and
    annealing the deposited film by heating it to an annealing temperature in the presence of a suitable oxidizing gas.

9. Method of producing a highly transparent electrically conducting metal film by laser directed chemical vapor deposition comprising positioning at least one suitable substrate within a deposition chamber, introducing into the chamber a suitable compound of a metallic element as a vapor;

irradiating a predetermined portion of the surface of the substrate with a laser beam having a wavelength selected to cause photochemical reduction of said compound so that said metallic element is deposited as a metal film on said predetermined portion of the substrate surface;

annealing the deposited film by heating it to an annealing temperature in the presence of a suitable oxidizing gas; and cycling anodic and cathodic electrical current through said film in an acid electrolyte bath.

10. The method of claim 9 wherein said bath is an aqueous sulfuric acid solution.

11. The method of claim 9 in which said annealing is carried out in air at a temperature of substantially 560-650 degrees C.

12. The method of claim 9 wherein said substrate includes a photosensitive semiconductor device and said transparent conductive metal film is selectively deposited thereover.

13. The method of claim 9 wherein said annealing is carried out until said film has a carbon content on the order of about 30% or less.

14. The method of claim 9 wherein said resulting metal film is formed with a structure having a multiplicity of voids that have a diameter on the order of 200 nonometers.

15. The method of claim 9 wherein said metal film is deposited to a thickness of at least 20 nanometers.

16. The method of claim 9 wherein said suitable compound it an organometallic compound which provides an adequate vapor pressure for deposition and which dissociates under action of said laser beam.

17. The method of claim 9 wherein said metallic element is either a noble or refractory metal.

18. The method of claim 17 wherein said metallic element is platinum.

19. The method of claim 17 wherein said suitable compound is allyl cyclopentadienyl platinum.

20. Method of producing a highly transparent electrically conducting metal film by laser directed chemical vapor deposition comprising positioning at least one suitable substrate within a deposition chamber;

introducing into the chamber a suitable compound of a metallic element as a vapor;

irradiating a predetermined portion of the surface of the substrate with a laser beam having a wavelength selected to cause photochemical reduction of said compound so that said metallic element is deposited as a metal film on said predetermined portion of the substrate surface; and annealing the deposited film by heating it to an annealing temperature in the presence of a suitable oxidizing gas;

wherein said substrate is transparent to said laser beam and is positioned at an entrance of said beam to the chamber, and the step of irradiating including directing said beam through the substrate to produce said metal film on a surface of the substrate from which the laser beam exits.

* * * * *